United States Patent
Dobson et al.

(10) Patent No.: US 8,880,450 B2
(45) Date of Patent: Nov. 4, 2014

(54) SYSTEMS AND METHODS FOR PREDICTING CHARACTERISTICS OF AN ARTIFICIAL HEART USING AN ARTIFICIAL NEURAL NETWORK

(75) Inventors: W. Kurt Dobson, Draper, UT (US); Ken Poppleton, Salt Lake City, UT (US)

(73) Assignee: World Heart Corporation, Salt Lake City, UT (US)

( * ) Notice: Subject to any disclaimer, the term of this patent is extended or adjusted under 35 U.S.C. 154(b) by 547 days.

(21) Appl. No.: 13/116,960

(22) Filed: May 26, 2011

(65) Prior Publication Data
US 2012/0303564 A1    Nov. 29, 2012

(51) Int. Cl.
*G06N 5/04* (2006.01)
*G06F 19/00* (2011.01)

(52) U.S. Cl.
CPC .......... *G06F 19/345* (2013.01); *G06F 19/3437* (2013.01)
USPC ......................................................... 706/45

(58) Field of Classification Search
USPC ......................................................... 706/45
See application file for complete search history.

(56) References Cited

U.S. PATENT DOCUMENTS

2004/0097782 A1* 5/2004 Korakianitis et al. ........... 600/16

* cited by examiner

*Primary Examiner* — Jeffrey A Gaffin
*Assistant Examiner* — Ola Olude Afolabi
(74) *Attorney, Agent, or Firm* — Lerner, David, Littenberg, Krumholz & Mentlik, LLP

(57) ABSTRACT

A system configured to predict characteristics of an artificial heart is described. The system includes a processor and memory in electronic communication with the processor, and an artificial neural network configured to receive an input vector of a predetermined length to train the artificial neural network, produce an output vector based on the input vector, and compare the output vector with a target vector of the predetermined length. When the output vector does not match the target vector within a predetermined error rate, the network is configured to adjust at least one weight, and when the output vector matches the target vector within the predetermined error rate, the network is configured to execute the input vector to produce an estimate at least one characteristic of the artificial heart.

32 Claims, 8 Drawing Sheets

SYSTEMS AND METHODS FOR PREDICTING CHARACTERISTICS OF AN ARTIFICIAL HEART USING AN ARTIFICIAL NEURAL NETWORK

BACKGROUND

Artificial heart pumps may be classified into the reciprocating type, the rotary displacement type, the centrifugal type, and the turbo type that operates by rotational flow. Artificial heart pumps of the centrifugal type may be equipped with a casing, a rotor disposed inside the casing, a motor for rotating the rotor, a blood flow channel for introducing and guiding the flow of blood, and an impeller that rotates integrally with the rotor for imparting centrifugal force to the blood flowing in through the blood flow channel formed in the casing.

Centrifugal type artificial hearts conventionally use ball bearings for rotatably supporting the rotor coupled with the impeller. In such configurations, blood flow is liable to stagnate in the vicinity of the ball bearing. An artificial heart pump that is susceptible to such stagnation may pose significant problems. The formation of stagnant blood is known to be a primary cause of blood coagulation. To eliminate this drawback, artificial heart pumps that include rotors suspended in a non-contacting state by magnetic forces have been used. These magnetically levitated heart pumps may constantly maintain the rotor in the proper attitude by regulating the current supplied to the electromagnets so as to control their magnetic field.

Prior efforts at developing a flow estimation method for artificial hearts, in an attempt to properly regulate the current supplied to the electromagnets, have focused on developing a linear equation describing the physics of the system, then using least-squared methods to find a best fit for the coefficients for the equation. These prior efforts, however, do not provide accurate estimates for magnetically levitated heart pumps because any dynamic force across the pump may perturb the position of the levitated rotor, which may change properties of the levitated pump. As a result, benefits may be realized by providing systems and methods for predicting characteristics of an artificial heart using an artificial neural network.

SUMMARY

According to at least one embodiment, a system configured to predict characteristics of an artificial heart is described. The system includes a processor and memory in electronic communication with the processor, and an artificial neural network configured to receive an input vector of a predetermined length to train the artificial neural network, produce an output vector based on the input vector, and compare the output vector with a target vector of the predetermined length. When the output vector does not match the target vector within a predetermined error rate, the network is configured to adjust at least one weight, and when the output vector matches the target vector within the predetermined error rate, the network is configured to execute the input vector to produce an estimate at least one characteristic of the artificial heart.

In one embodiment, the artificial heart is an artificial heart having at least one magnetically levitated component. In one example, the at least one characteristic of the artificial heart may be positive fluid flow produced by the artificial heart. In another example, the at least one characteristic of the artificial heart may be negative fluid flow produced by the artificial heart. The at least one characteristic of the artificial heart may also be differential pressure exhibited across an inlet and an outlet of the artificial heart. The at least one characteristic of the artificial heart may also be a pulsitility index. In one embodiment, the artificial neural network may predict a condition of a patient that uses the artificial heart.

In one configuration, the input vector may include at least one of rotor speed, rotor position, or motor current of the artificial heart. The input vector may also include at least one of levitation current, system current, or system voltage. In one embodiment, the artificial heart may be a left ventricular assist device (LVAD). In one example, the artificial heart may be a right ventricular assist device (RVAD).

A computer-implemented method to predict characteristics of an artificial heart using an artificial neural network is also described. An input vector of a predetermined length may be received to train the artificial neural network. An output vector may be produced based on the input vector. The output vector may be compared with a target vector of the predetermined length. When the output vector does not match the target vector within a predetermined error rate, at least one weight of the artificial neural network may be adjusted. When the output vector matches the target vector within the predetermined error rate, the artificial neural network may execute the input vector to produce an estimate at least one characteristic of the artificial heart.

A computer-program product for predicting characteristics of an artificial heart using an artificial neural network is also described. The computer-program product may include a non-transitory computer-readable medium having instructions thereon. The instructions may include code programmed to receive an input vector of a predetermined length to train the artificial neural network, and code programmed to produce an output vector based on the input vector. The instructions may further include code programmed to compare the output vector with a target vector of the predetermined length. When the output vector does not match the target vector within a predetermined error rate, the instructions may include code programmed to adjust at least one weight. When the output vector matches the target vector within the predetermined error rate, the instructions may include code programmed to execute the input vector to produce an estimate at least one characteristic of the artificial heart.

A system configured to predict conditions of a patient using an artificial heart is also described. The system may include a processor and memory in electronic communication with the processor. The system may further include an artificial neural network configured to receive an input vector of a predetermined length to train the artificial neural network, and produce an output vector based on the input vector. The artificial neural network may be further configured to compare the output vector with a target vector of the predetermined length. When the output vector does not match the target vector within a predetermined error rate, the artificial neural network may be configured to adjust at least one weight. When the output vector matches the target vector within the predetermined error rate, the artificial neural network may be configured to execute the input vector to produce an estimate of at least one condition of the patient using the artificial heart.

In one configuration, the patient may use a natural heart in conjunction with the artificial heart. The at least one condition of the patient may be hematocrit properties of the patient. In one example, the at least one condition of the patient may be a pulsitility index of the blood of the patient. The pulsitility index may describe the strength of a natural heart of the patient being used in conjunction with the artificial heart.

In one configuration, the at least one condition of the patient may be blood viscosity properties of the patient. The at least one condition of the patient may be a recovery measurement of the natural heart of the patient. In one embodiment, the recovery measurement may be a measurement of the contractility of a native ventricle of the natural heart of the patient. In one example, the recovery measurement may be a measurement of the elastance of a native ventricle of the natural heart of the patient.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

Figure 1:
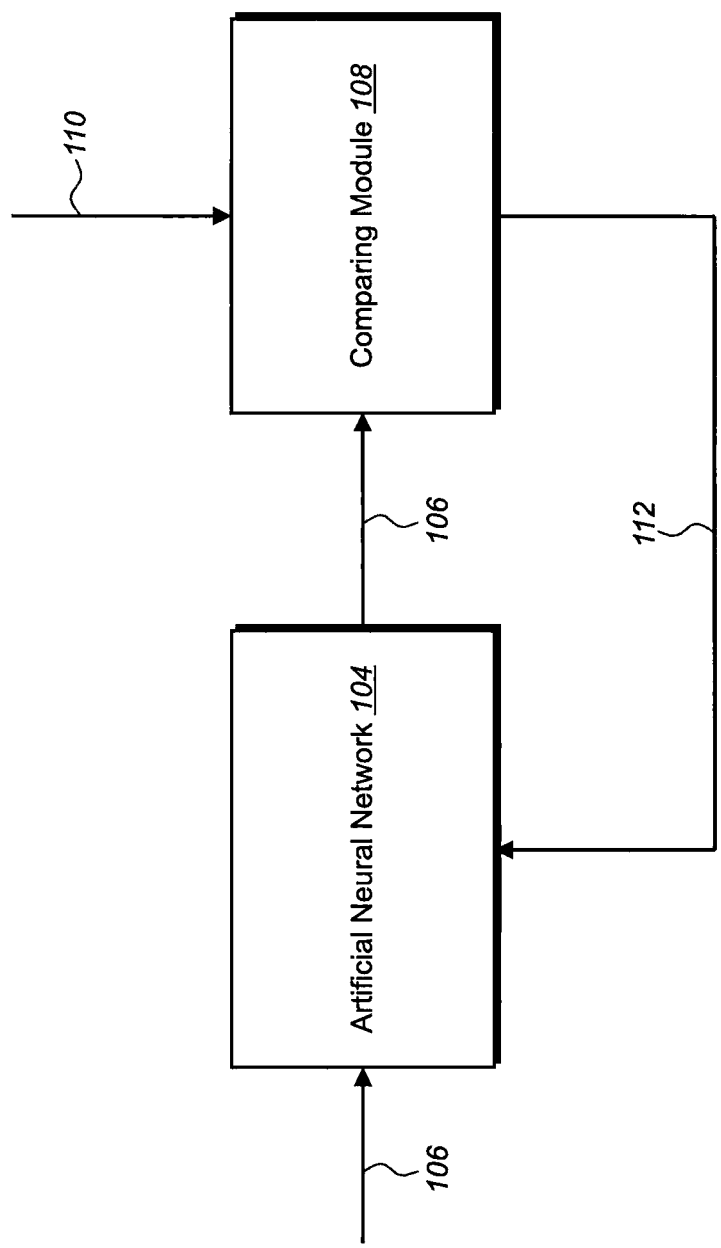
FIG. 1 is a block diagram illustrating one embodiment of an environment in which the present systems and methods may be implemented.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

An artificial heart is a mechanical device that may replace the heart of a human or other mammal. An artificial heart may be used to bridge the time to heart transplantation, or to permanently replace the heart in the case that transplantation is not possible. Although the heart is conceptually simple (basically a muscle that functions as a pump), the heart embodies subtleties that may defy straightforward emulation with synthetic materials and power supplies. Consequences of these issues may include severe foreign-body rejection and external power sources that limit patient mobility.

Further, the development of artificial hearts may require the developers to accurately estimate certain characteristics of the artificial heart. For example, developers may desire to accurately estimate flow, differential pressure, and hematocrit properties of an artificial heart. In addition, developers may desire to accurately predict the orientation (e.g., standing up, lying down, inclined, etc.) of a patient that is using an artificial heart.

A ventricular assist device (VAD) is a mechanical circulatory device that may be used to partially or completely replace the function of a failing heart. A VAD may be used for a short time period (e.g., during a recovery period following a heart attack or heart surgery). A VAD may be used for a long time period (e.g., for patients suffering from congestive heart failure. In one embodiment, VADs may be designed to assist either the right (RVAD) or left (LVAD) ventricle. Long term VADs may be used to keep patients alive with an acceptable quality of life while they wait for heart transplantation. LVADs, however, may be used as destination therapy and sometimes as a bridge to recovery.

The term artificial heart, as used herein, may refer to an artificial heart device that typically takes over the cardiac function of a heart. The term artificial heart, as used herein, may also refer to VADs, for example, the RVAD and the LVAD.

Prior efforts at developing flow estimation for artificial hearts have focused on developing a linear equation that may describe the physics of the system (i.e., patient and artificial heart). These previous efforts may then use a least-square method to find a best fit for the coefficients for the developed linear equation. As a result, prior efforts have focused on the "system identification" problem, where it is desired to develop a model that describes (predicts) the function of a device. For non-trivial systems with non-linear properties and unknown coupling mechanisms, developing a direct equation may be difficult, employing trial and error methods. A non-linear neural network is known to find the underlying model, regardless of the nonlinearity, coupling mechanisms given sufficient "Shannon" information in the input space, along with an adequate topology for the neural network.

A magnetically levitated artificial heart may include a rotor and impeller that are suspended with no support other than magnetic fields. These components may be suspended by constantly altering the strength of a magnetic field produced by electromagnets. Magnetic levitation may reduce the energy consumption of the artificial heart. In addition, the energy efficiency of the artificial heart may be increased by minimizing the contact points between frictional surfaces. Flow estimation processes used in prior efforts, however, may not provide adequate estimations when used with an artificial heart employing magnetic levitation. Dynamic forces across the artificial heart (e.g., the left ventricle), may perturb the position of the levitated rotor. This may change the magnetic coupling, the volume of the pumping chamber, and the resulting shear forces on blood. In one configuration, magnetically levitated components of an artificial heart may have no bearing surfaces. This may provide many hemocompatibility benefits including, but not limited to, lower thrombus, stroke, and heart attack events.

In one embodiment, the present systems and methods may use an artificial neural network to determine a direct equation that describes a magnetically levitated artificial heart operating in a patient. In one example, artificial neural networks may include interconnecting artificial neurons (programming constructs that may emulate the properties of biological neurons). In one configuration, artificial neural networks may either be used to gain an understanding of biological neural networks, or for solving artificial intelligence problems without necessarily creating a model of a real biological system. Artificial neural networks may be a tool to extract a direct model of one or more unknown systems. Further, if an artificial neural network converges to some error tolerance, the input data may suffice to adequately and correctly describe such a system. The particular implementation of an artificial neural network used by the present systems and methods may solve linear or nonlinear transforms from the input data (such as vectors) to the prediction (estimation) space.

The present systems and methods may use artificial neural network architecture to accurately estimate, for example, flow rates, pump differential pressure, and hematocrit properties of a magnetically levitated artificial heart. The artificial neural network may also accurately predict the orientation of a patient that may have the artificial heart installed in his/her body. The algorithm resulting from the artificial neural network may predict both positive and negative flow, pump differential, pressure, and viscosity (hematocrit) based on indirect signals controlling the artificial heart. Examples of inputs of these indirect signals may include, but is not limited to, rotor speed, motor current, levitation current, system current, and system voltage.

FIG. 1 is a block diagram illustrating one embodiment of an environment in which the present systems and methods may be implemented. In one example, an artificial neural network 104 may receive at least one input 102. The artificial neural network 104 may be used to determine an equation that describes a system, such as a magnetically levitated heart. In one embodiment, the artificial neural network 104 may include elements operating in parallel. The function of the network 104 may be determined by the connections (weights) between these elements. The artificial neural network 104 may be trained to perform a particular function by adjusting the values of the connections (weights) between the elements.

The artificial neural network 104 may generate an output 106 that may be compared to a target output 110. The output 106 and the target output 110 may be compared by a comparing module 108. If the output 106 does not satisfy an error threshold when compared to the target output 110, adjusted weights 112 may be applied to the artificial neural network 104. The adjusted weights 112 may adjust the output 106 generated by the artificial neural network 104. The artificial neural network 104 may be adjusted by the adjusted weights 112 until the output 106 satisfies the error threshold when compared to the target output 110. As a result, the artificial neural network 104 may be adjusted (or trained) so that a particular input 102 leads to a specific output 106. The network may be adjusted by the adjusted weights 112 based on a comparison of the output 106 and the target output 110. The network 104 may be adjusted until the output 106 matches the target output 110.

In one configuration, the artificial neural network 104 may be batch trained. Batch training may include providing adjusted weights 112 and bias changes based on an entire batch (set) of input vectors. Incremental training may adjust the weights and biases of the network 104 after a presentation of each individual input vector 102. Incremental training may be referred to as "on line" or "adaptive" training.

As explained above, the artificial neural network 102 may be trained to perform complex functions in various fields, including, but not limited to, pattern recognition, identification, classification, speech, vision, and control systems. The artificial neural network 102 may be trained to solve problems that are difficult for conventional computers or human beings.

Supervised training (as described above) may be used, but other artificial neural networks may be obtained from unsupervised training techniques or from direct design methods where training may not be required. In one embodiment, unsupervised artificial neural networks may be used, for example, to identify groups of data. Certain kinds of networks may be designed directly. As a result, there are a variety of designs and training techniques for developers of the artificial neural network 104.

Figure 2:
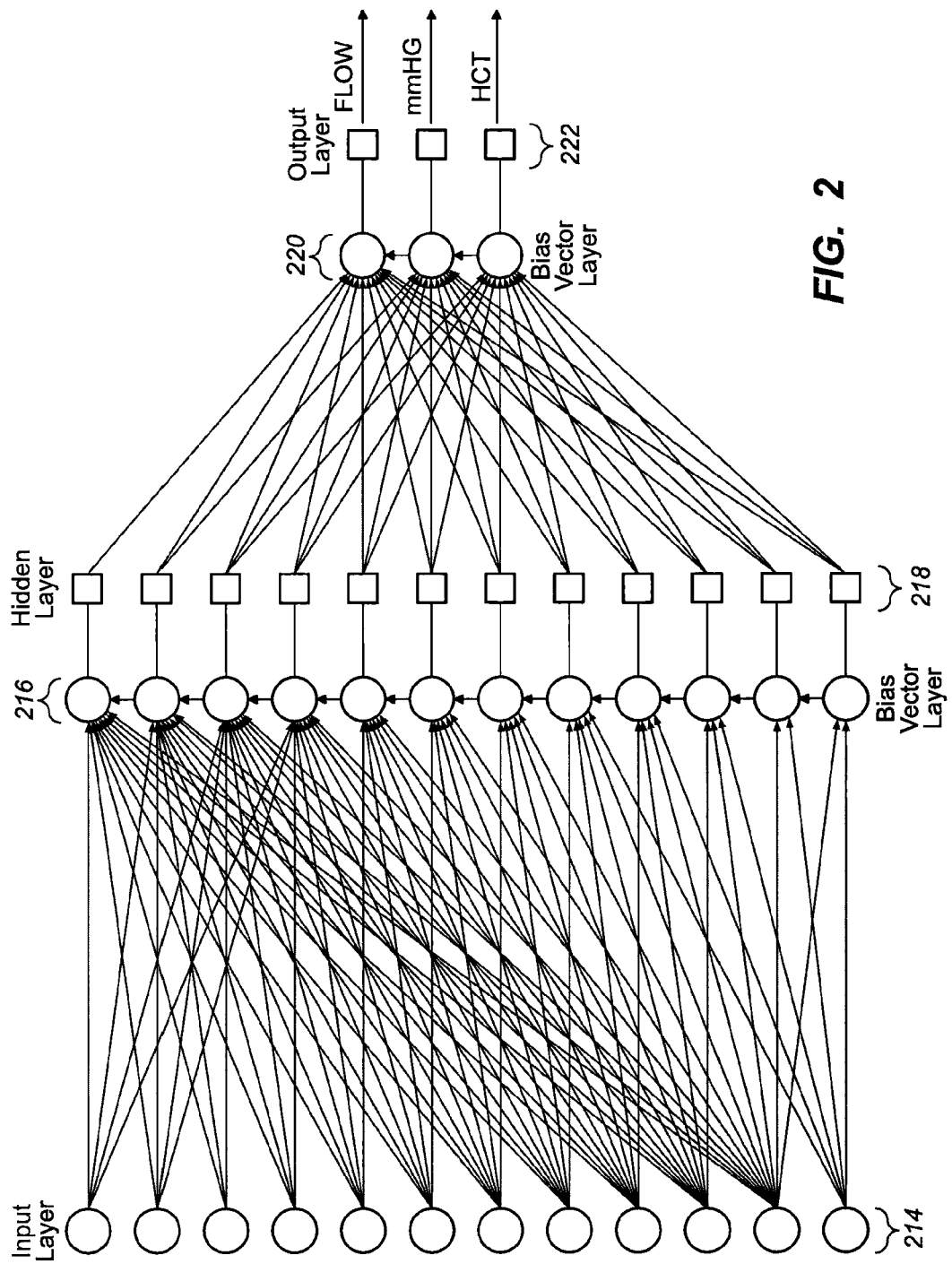
FIG. 2 is a block diagram illustrating one embodiment of an artificial neural network that may be implemented in the present systems and methods.

FIG. 2 is a block diagram illustrating one embodiment of the artificial neural network 104 that may be implemented in the present systems and methods. The network 104 may be trained to provide estimates for certain characteristics of an artificial heart. For example, the network 104 may provide estimates for flow rates, differential pressure, and hematocrit properties of the artificial heart. In addition, the network 104 may predict the orientation of the patient that is using the artificial heart.

In one configuration, the network 104 may include an input layer 214, a hidden bias vector layer 216, a hidden layer 218, an output bias vector layer 220, and an output layer 222. In one configuration, an input data set (vector) that includes a plurality of samples of input data may be input 102 to the artificial neural network 104 (see FIG. 1) at the input layer 214. Input data sets at the input layer 214 may be summed with a bias vector included in the hidden bias vector layer 216. In one example, a transfer function may be applied to the output from a bias vector in the hidden bias vector layer 216. An example of the transfer function may be the following:

$$\tan sig(x) = \frac{2}{(1+e^{-2x})-1} \quad \text{Equation 1}$$

Figure 3:
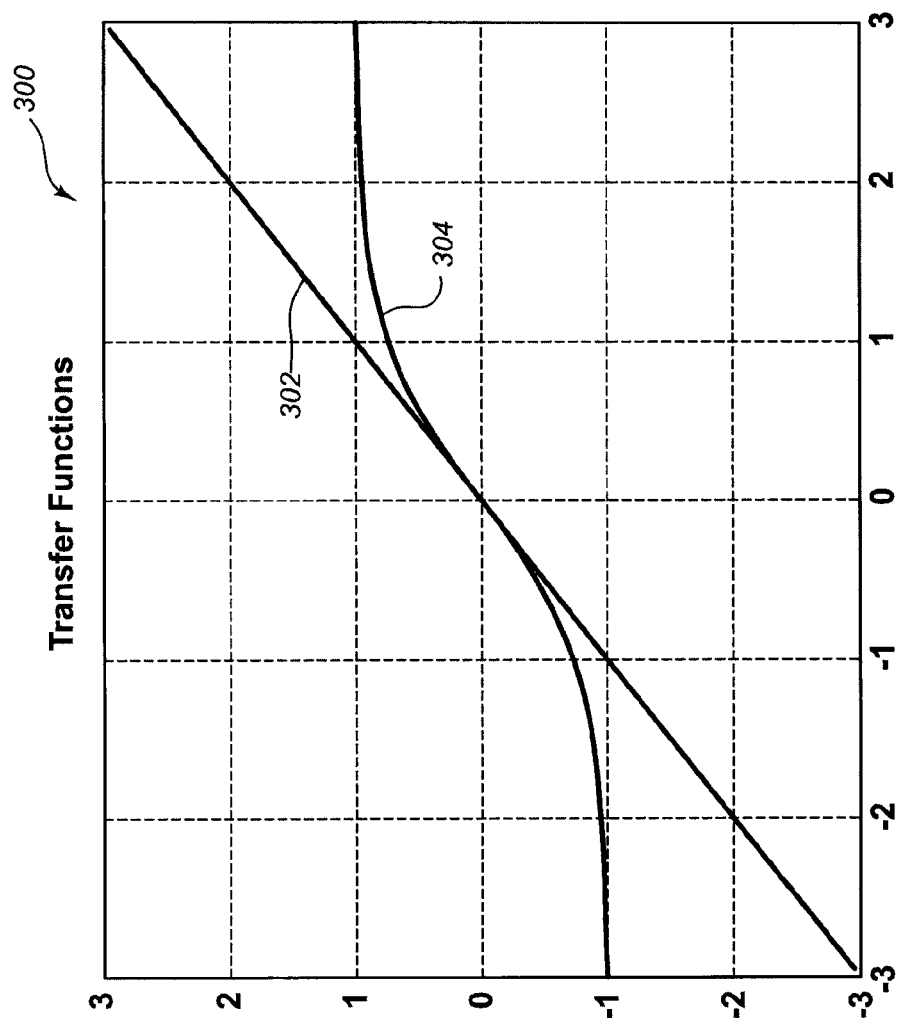
FIG. 3 is a block diagram illustrating multiple transfer functions in accordance with the present systems and methods.

FIG. 3 is a graph 300 illustrating one embodiment of multiple transfer functions. In one configuration, the graph 300 includes a nonlinear transfer function 302, such as the tansig function listed as Equation 1 above, and a linear transfer function 304.

The output from a neuron included in the hidden layer 218 may be summed with a bias vector included in the output bias vector layer 220. In one configuration, the output layer 222 may apply a pure linear function to the output from the output bias layer 220. The output of the output layer 222 may include flow estimates, differential pressure estimates, and hematocrit estimates. An example equation representing the output may be:

$$y = purelin[\sum_{k=1}^{N}] \left[ \tan sig \left[ \sum_{k=1}^{N} \lceil (I_k \cdot Wa_k) + ba \rceil \right] \cdot Wb_k \right] + bb \quad \text{Equation 2}$$

In Equation 2, "y" may be the output, "I" may be the input vector, "Wa" may be the hidden matrix, "Wb" may be the output matrix, "ba" may be the hidden bias vector, and "bb" may be the output bias vector. In one embodiment, "tansig" may be the nonlinear operator that is an approximation to "tan h", defined as:

$$\tan hx = \frac{\sin hx}{\cos hx} = \frac{e^x - e^{-x}}{e^x + e^{-x}} = \frac{e^{2x}-1}{e^{2x}+1} \quad \text{Equation 3}$$

In one embodiment, the network 104 may be trained, validated, and tested by providing an input data set including six columns each of approximately 81,000 samples of input data. A target vector of the same length may be prepared with the corresponding flow and delta pump pressure data. In one configuration, flow training data may be provided by an ultrasonic flow measuring system. Pressure data may be provided from pressure transducers. Data available as inputs for training the artificial neural network 104 may include rotor rpm, rotor position, motor current, levitation current, system current, and system voltage of an artificial heart. In one example, additional inputs may include (rotor speed)$^2$ (i.e., inertia), (rotor speed)*(rotor position), a derivative of rotor speed, a derivative of rotor position, and a derivative of levitation current of the artificial heart.

Using the above referenced inputs for training, the size of a matrix to train the network 104 may be, but is not limited to, 11 columns×the number of training samples (approximately 81,000) samples. The training algorithm may also use time information in the flow and pressure estimations. In one example, four additional time shifts may be used for the input matrix in the algorithm. As a result, the size of the training matrix may be 55 (5×11)×the 81,000 samples mentioned above. In one embodiment, the target matrix may be two columns. A first column may include the ultrasonic flow measurement for each input state. A second column may include the differential pressure measurements as instrumented.

In one embodiment, the artificial neural network 104 may be created with approximately (but not limited to) 55 neurons in the input layer 214 (only 12 neurons shown for sake of simplicity and clarity) and three linear output neurons (flow rate, differential pressure, and hematocrit estimates). The input layer 214 may use the nonlinear tansig transfer function provided above as Equation 1. The output layer 222 may be a pure linear function. The network 104 may converge to solve linear or nonlinear functions between the inputs and outputs to some error bounded by the complexity of the network 104 (e.g., number of neurons). In one configuration, training of the artificial neural network 104 may be performed using the Levinburg Marquardt gradient descent method. This method may provide a numerical solution to the problem of minimizing a function, generally nonlinear, over a space of parameters of the function.

After the network 104 has been trained, it may be run on the entire data set. In one configuration, the flow prediction error may be 0.0595 liters/minute in the positive flow region and 0.1861 liters/minute in the negative flow region. In one embodiment, the flow prediction in the negative flow region may be affected by the ultrasonic flow measurement in the negative direction. In one embodiment, two back to back flow transducers may be used to obtain training data for negative flow estimation. In addition, pressure data may be used to calculate flow estimation. Pressure data to calibrate transonic data may be used when a bypass valve of the artificial heart is open on the loop.

In one configuration, data on a particular known pump may be gathered where hematocrit was known. The network 104 may include a third output for hematocrit predictions. In order to estimate hematocrit, the number of columns of the matrix described above may be increased to 65×65. With the larger matrix, the errors for the predictions of flow, differential pressure, and hematocrit may be close to zero.

In one example, an input vector may be provided as the input to the network. In one embodiment, the input vector may include 65 input neurons. The input layer may include control information, derivatives, squares, etc. as well as the time shifted version of the indirect data. The hidden layer may also include 65 neurons. The output of the hidden layer may be formed by a nonlinear operator over the sum of the weight matrix plus a bias vector. The weights and biases may be solved through a gradient descent method, such as the Levinburg Marquardt gradient descent method. The artificial neural network of the present systems and methods may include at least three output neurons with a linear output operator (e.g., pure linear function). The three output neurons (one for each of the predicted functions) may be formed by a linear operator over the sum of inputs (from the hidden layer), and a bias. The weights and biases may be solved simultaneously with the hidden layer weights and biases using the gradient descent method described above.

In one embodiment, the artificial neural network 104 of the present systems and methods may include an input vector of 65 neurons and a hidden layer of 65 neurons. The inner layer may be solved in 65 multiply adds followed by 65 nonlinear tansig( ) operations. For each of the three output neurons, the output may be solved with a 65×1 multiply add followed by a purelin( ) transform.

In one configuration, the artificial neural network 104 of the present systems and methods may be trained by presenting input vectors and target vectors, taking the error between the two, and using an efficient gradient descent method (e.g., Levinburg Marquardt) that may result in two internal matrices converging such that the input space may match the target vector space under all operating conditions. The resulting inner matrix (from the convergence of the two internal matrices) may be 65×65.

Figure 4:
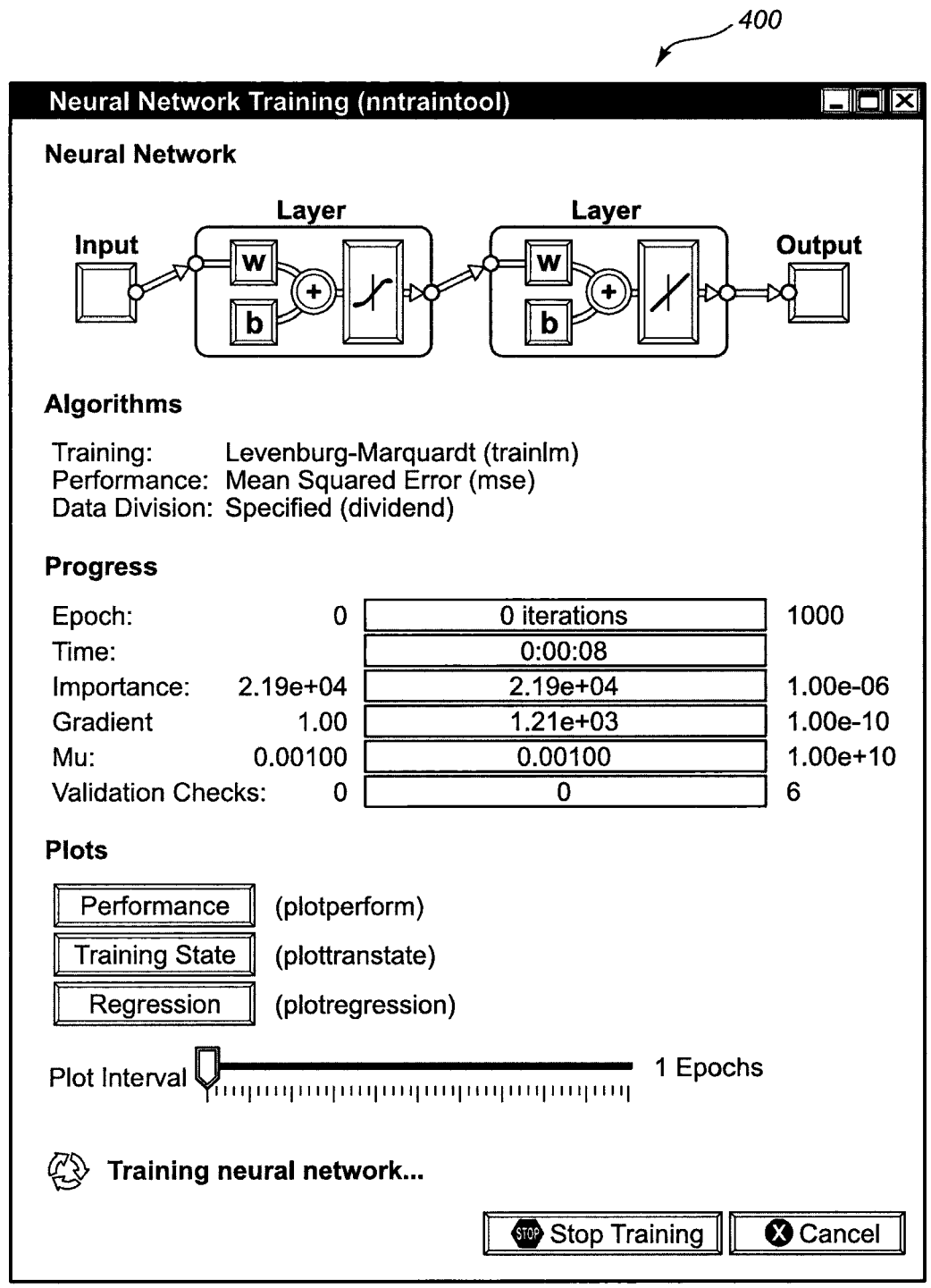
FIG. 4 is a screen shot of a user interface illustrating one embodiment of a training tool interface for the artificial neural network.

FIG. 4 is a screen shot of a user interface illustrating one embodiment of a training tool interface 400 for the artificial neural network 104. The tool 400 may provide a simplified matrix model for the artificial neural network 104. In addition, the tool 400 may allow the training, validation, and testing of the artificial neural network 104 to be done in parallel. Further, the tool 400 may allow for automatic stops on gradient and validation thresholds.

Figure 5:
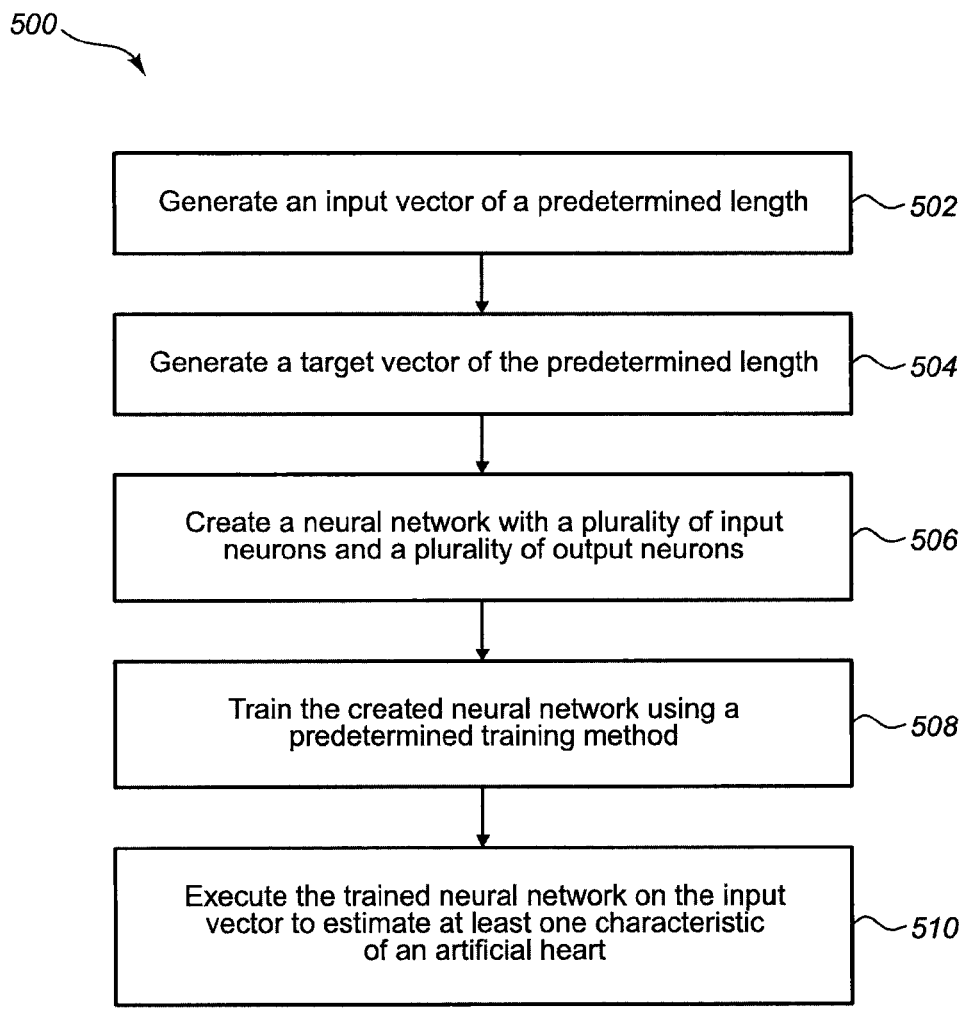
FIG. 5 is a flow diagram illustrating one embodiment of a method to predict characteristics of an artificial heart.

FIG. 5 is a flow diagram illustrating one embodiment of a method 500 to predict characteristics of an artificial heart. In one example, the artificial heart may be a magnetically levitated artificial heart. In one embodiment, the method 500 may be implemented by the artificial neural network 104.

In one configuration, an input vector of a predetermined length may be generated 502. A target vector of the predetermined length may also be generated 504. In one example, the artificial neural network 104 may be created 506 with a plurality of input neurons and a plurality of output neurons. The created artificial neural network may be trained 508 using a predetermined training method. For example, the input vector may be input to the network 104 and the output of the network 104 may be compared against the target vector. One or more connections between the input neurons may be adjusted until the output of the network 104 matches the target vector with a certain degree of accuracy. In one configuration, the trained artificial neural network 104 may be executed on the input vector to estimate at least one characteristic of an artificial heart. For example, the network 104 may estimate flow rates, differential pressure, hematocrit, patient orientation or some combination of such characteristics. In one configuration, the network 104 may also compute a pulsitility index. The pulsitility index may be a measure of the variability of blood velocity in a vessel, equal to the difference between the peak systolic and minimum diastolic velocities divided by the mean velocity during a cardiac cycle.

Figure 6:
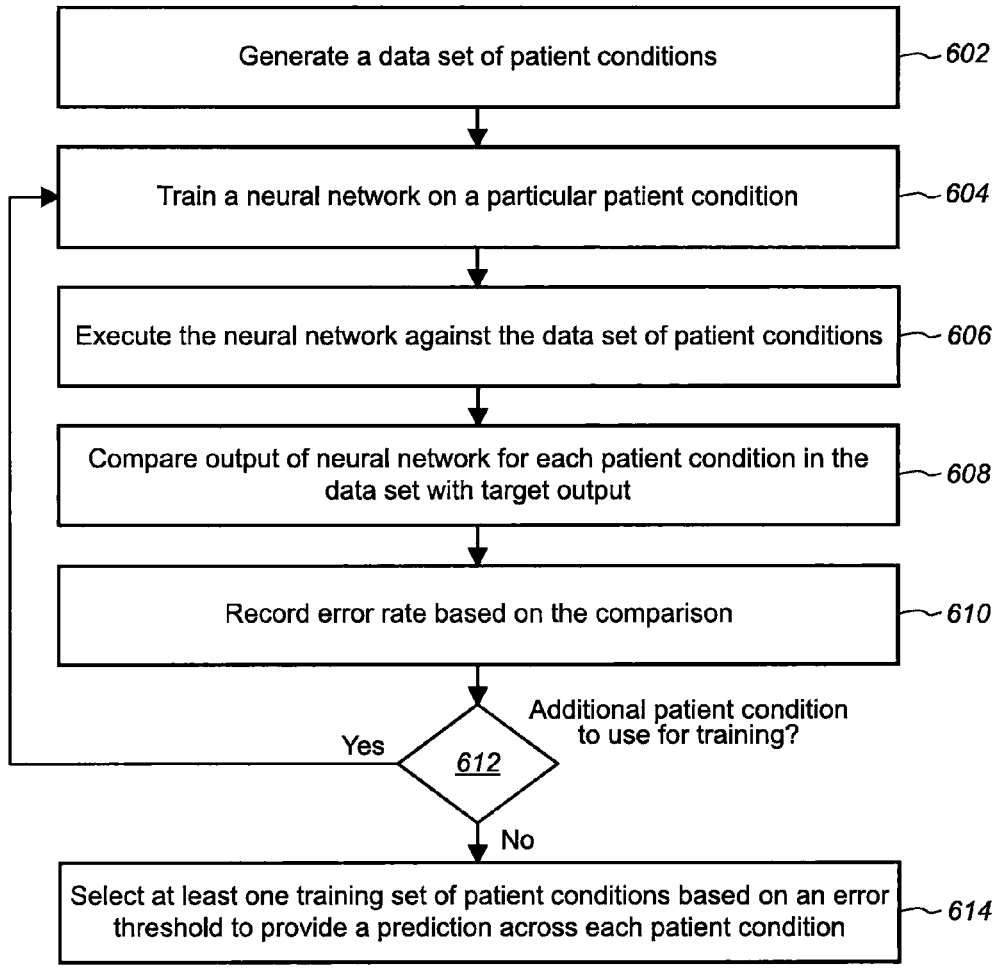
FIG. 6 is a flow diagram illustrating one embodiment of a method to predict conditions of a patient who has an artificial heart.

FIG. 6 is a flow diagram illustrating one embodiment of a method 600 to predict conditions of a patient who has an artificial heart. In one configuration, the method 600 may be implemented by the artificial neural network 104. To predict patient conditions, corners of the test data may be found in non-linear space.

In one configuration, a data set of patient conditions may be generated 602. The artificial neural network 104 may be trained 604 on a particular patient condition. The network 104 may be executed 606 against the data set of patient conditions. The output of the network 104 for each patient condition in the data set may be compared 608 with target output. An error rate based on the comparison may be recorded 610. In one embodiment, a determination 612 may be made as to whether additional patient conditions exist to use for training. If it is determined 612 that additional patient conditions exist, the method 600 may return to train the network 104 on the additional patient conditions including, for example, the execution of acts 604 through 610. If, however, it is determined 612 that additional patient conditions do not exist to use for training, at least one training set of patient conditions may be selected 614. The at least one selected set of conditions may be selected based on an error threshold to provide a prediction across each patient condition.

In one configuration, for each patient condition C(k), the artificial neural network 104 may be trained on C(k). The network 104 may be tested against all C(k)'s and the errors may be recorded. In one example, the errors may be sorted (e.g., lowest to highest). A histogram of error between the trained set of conditions and the test set may indicate linear or non-linear space between the two spaces. In one embodiment, N training sets may be selected based on the desired error threshold for predictions across all the patient conditions. In one embodiment, the patient conditions may include, but are not limited to, combinations of analog left ventricle (LV) rate, LV drive pressure, venous reservoir head, mean systemic pressure, systemic compliance, etc.

In one configuration, the patient may use a natural heart in conjunction with an artificial heart. The patient conditions that may be estimated by the neural network may further include hematocrit properties of the patient and a pulsitility index of the blood of the patient. In one configuration, the pulsitility index may describe the strength of a natural heart of the patient being used in conjunction with the artificial heart. Additional conditions of the patient that may be estimated by the neural network may include blood viscosity properties of the patient and a recovery measurement of the natural heart of the patient. In one embodiment, the recovery measurement may be a measurement of the contractility of a native ventricle of the natural heart of the patient. The recovery measurement may also be a measurement of the elastance of a native ventricle of the natural heart of the patient.

As described above, the present systems and methods provide accurate estimates for flow, differential pressure, hematocrit, and patient orientations/conditions using an artificial neural network architecture. The present systems and methods may predict both positive and negative flow, pump differential pressure, and viscosity (hematocrit) based on indirect signals controlling the artificial heart. The artificial heart may include at least one magnetically levitated component. As mentioned above, inputs may include, but are not limited to rotor speed, rotor position, motor current, levitation current, system current, and system voltage.

The artificial neural network may be trained and tested with simulated patient conditions on a mock circulatory system. In one embodiment, training of the neural network may be performed at the "corners" of the patient conditions simulated on the mock circulatory system. Testing may be performed on samples of patient conditions throughout a range of possible patient conditions on the mock circulatory system.

Figure 7:
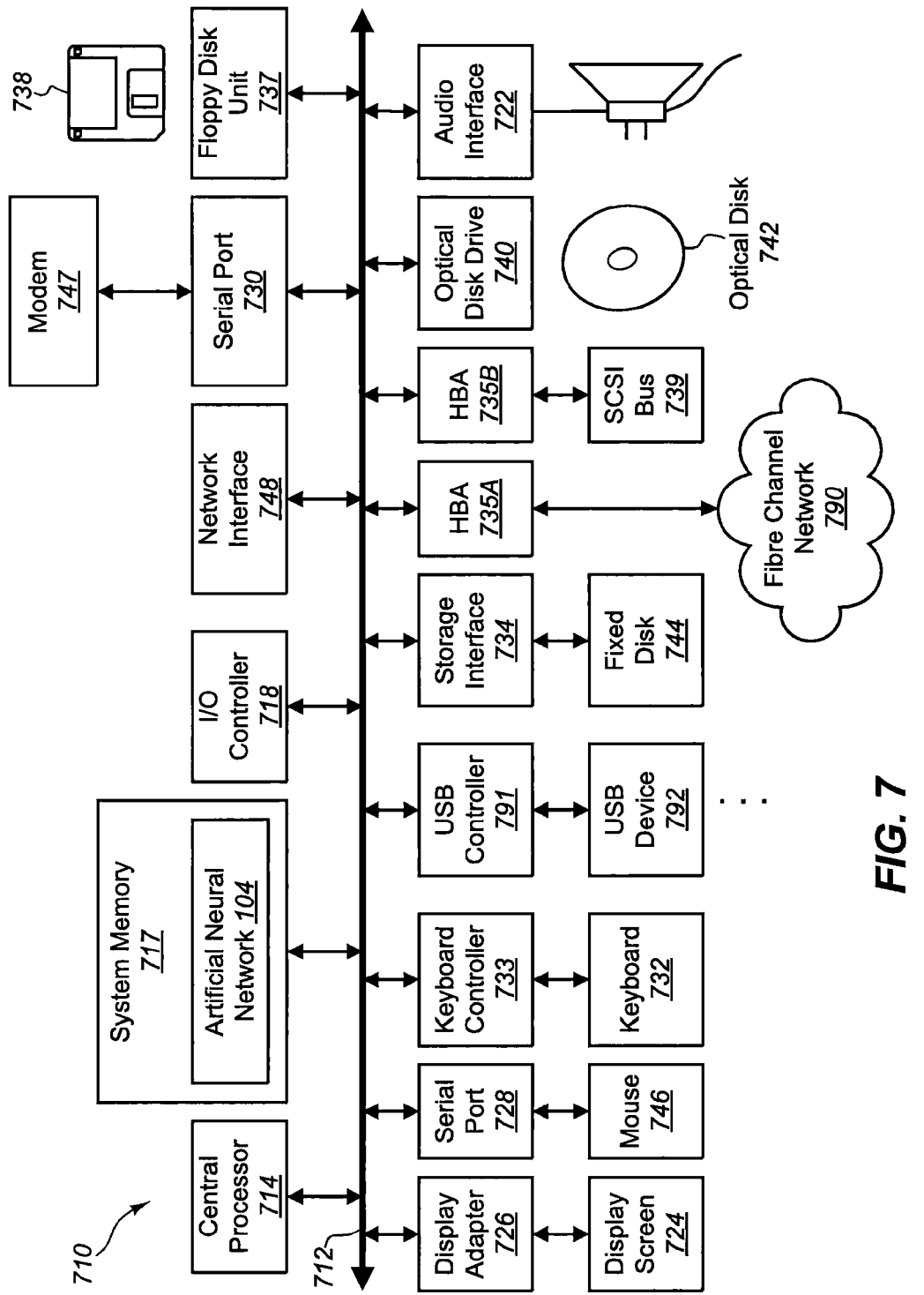
FIG. 7 depicts a block diagram of a computer system suitable for implementing the present systems and methods.

FIG. 7 depicts a block diagram of one example of a computer system 710 suitable for implementing the present systems and methods. Computer system 710 includes a bus 712 which interconnects major subsystems of computer system 710, such as a central processor 714, a system memory 717 (typically RAM, but which may also include ROM, flash RAM, or the like), an input/output controller 718, an external audio device, such as a speaker system 720 via an audio output interface 722, an external device, such as a display screen 724 via display adapter 726, serial ports 728 and 730, a keyboard 732 (interfaced with a keyboard controller 733), multiple USB devices 792 (interfaced with a USB controller 790), a storage interface 734, a floppy disk drive 737 operative to receive a floppy disk 738, a host bus adapter (HBA) interface card 735A operative to connect with a Fibre Channel network 790, a host bus adapter (HBA) interface card 735B operative to connect to a SCSI bus 739, and an optical disk drive 740 operative to receive an optical disk 742. Also included are a mouse 746 (or other point-and-click device, coupled to bus 712 via serial port 728), a modem 747 (coupled to bus 712 via serial port 730), and a network interface 748 (coupled directly to bus 712).

Bus 712 allows data communication between central processor 714 and system memory 717, which may include read-only memory (ROM) or flash memory (neither shown), and random access memory (RAM) (not shown), as previously noted. The RAM is generally the main memory into which the operating system and application programs are loaded. The ROM or flash memory can contain, among other code, the Basic Input-Output system (BIOS) which controls basic hardware operation such as the interaction with peripheral components or devices. For example, the artificial neural network 104 to implement the present systems and methods may be stored within the system memory 717. Applications resident with computer system 710 are generally stored on and accessed via a computer readable medium, such as a hard disk drive (e.g., fixed disk 744), an optical drive (e.g., optical drive 740), a floppy disk unit 737, or other storage medium. Additionally, applications can be in the form of electronic signals modulated in accordance with the application and data communication technology when accessed via network modem 747 or interface 748.

Storage interface 734, as with the other storage interfaces of computer system 710, can connect to a standard computer readable medium for storage and/or retrieval of information, such as a fixed disk drive 744. Fixed disk drive 744 may be a part of computer system 710 or may be separate and accessed through other interface systems. Modem 747 may provide a direct connection to a remote server via a telephone link or to the Internet via an internet service provider (ISP). Network interface 748 may provide a direct connection to a remote server via a direct network link to the Internet via a POP (point of presence). Network interface 748 may provide such connection using wireless techniques, including digital cellular telephone connection, Cellular Digital Packet Data (CDPD) connection, digital satellite data connection or the like.

Many other devices or subsystems (not shown) may be connected in a similar manner (e.g., document scanners, digital cameras and so on). Conversely, all of the devices shown in FIG. 7 need not be present to practice the present systems and methods. The devices and subsystems can be interconnected in different ways from that shown in FIG. 7. The operation of a computer system such as that shown in FIG. 7 is readily known in the art and is not discussed in detail in this application. Code to implement the present disclosure can be stored in computer-readable medium such as one or more of system memory 717, fixed disk 744, optical disk 742, or floppy disk 738. The operating system provided on computer system 710 may be MS-DOS®, MS-WINDOWS®, OS/2®, UNIX®, Linux®, or another known operating system.

Moreover, regarding the signals described herein, those skilled in the art will recognize that a signal can be directly transmitted from a first block to a second block, or a signal can be modified (e.g., amplified, attenuated, delayed, latched, buffered, inverted, filtered, or otherwise modified) between the blocks. Although the signals of the above described embodiment are characterized as transmitted from one block to the next, other embodiments of the present systems and methods may include modified signals in place of such directly transmitted signals as long as the informational and/or functional aspect of the signal is transmitted between blocks. To some extent, a signal input at a second block can be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

Figure 8:
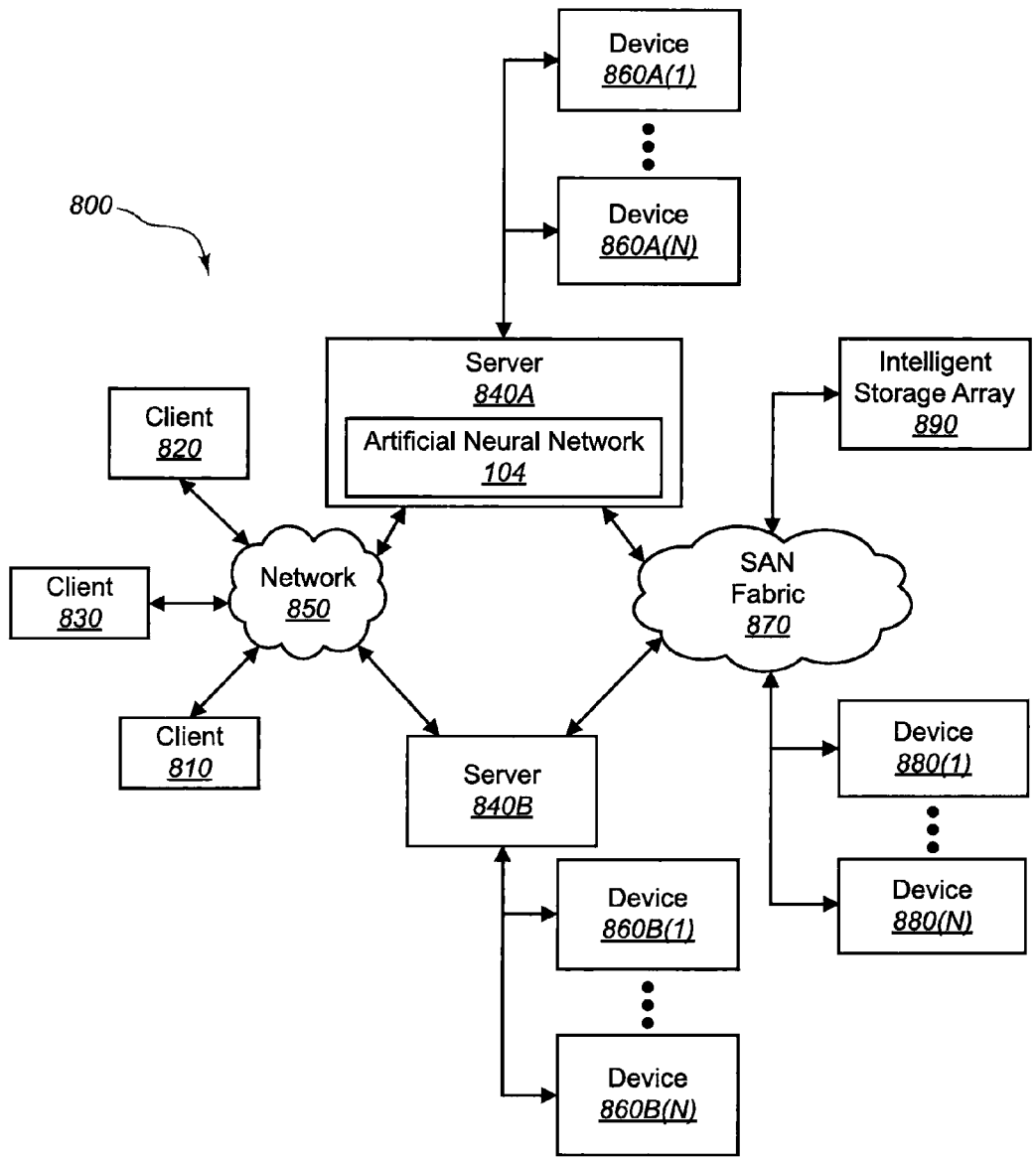
FIG. 8 is a block diagram depicting a network architecture in which client systems, as well as storage servers (any of which can be implemented using computer system), are coupled to a network.

FIG. 8 is a block diagram depicting a network architecture 800 in which client systems 810, 820 and 830, as well as storage servers 840A and 840B (any of which can be implemented using computer system 810), are coupled to a network 850. In one embodiment, the artificial neural network 104 may be located within a server 840A, 840B to implement the present systems and methods. The storage server 840A is further depicted as having storage devices 860A(1)-(N) directly attached, and storage server 840B is depicted with storage devices 860B(1)-(N) directly attached. SAN (storage area network) fabric 870 supports access to storage devices 880(1)-(N) by storage servers 840A and 840B, and so by client systems 810, 820, and 830 via network 850. Intelligent storage array 890 is also shown as an example of a specific storage device accessible via SAN fabric 870.

With reference to computer system 710, modem 747, network interface 748 or some other method can be used to provide connectivity from each of client computer systems 810, 820, and 830 to network 850. Client systems 810, 820, and 830 are able to access information on storage server 840A or 840B using, for example, a web browser or other client software (not shown). Such a client allows client systems 810, 820, and 830 to access data hosted by storage server 840A or 840B or one of storage devices 860A(1)-(N), 860B(1)-(N), 880(1)-(N) or intelligent storage array 890. FIG. 8 depicts the use of a network such as the Internet for exchanging data, but the present systems and methods are not limited to the Internet or any particular network-based environment.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered exemplary in nature since many other architectures can be implemented to achieve the same functionality.

The process parameters and sequence of acts described and/or illustrated herein are given by way of example only and can be varied as desired. For example, while the acts illustrated and/or described herein may be shown or discussed in a particular order, these acts do not necessarily need to be performed in the order illustrated or discussed. The various exemplary methods described and/or illustrated herein may also omit one or more of the acts described or illustrated herein or include additional acts in addition to those disclosed.

Furthermore, while various embodiments have been described and/or illustrated herein in the context of fully functional computing systems, one or more of these exemplary embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the exemplary embodiments disclosed herein.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present systems and methods and their practical applications, to thereby enable others skilled in the art to best utilize the present systems and methods and various embodiments with various modifications as may be suited to the particular use contemplated.

Unless otherwise noted, the terms "a" or "an," as used in the specification and claims, are to be construed as meaning "at least one of." In addition, for ease of use, the words "including" and "having," as used in the specification and claims, are interchangeable with and have the same meaning as the word "comprising."

What is claimed is:

1. A system configured to predict characteristics of an artificial heart, comprising:
   a processor;
   memory in electronic communication with the processor and
   an artificial neural network in communication with the artificial heart, the artificial neural network being configured to:
   receive an input vector of a predetermined length to train the artificial neural network;
   produce an output vector based on the input vector;
   compare the output vector with a target vector of the predetermined length;
   when the output vector does not match the target vector within a predetermined error rate, adjust at least one weight;
   when the output vector matches the target vector within the predetermined error rate, execute the input vector to produce an estimate of at least one of a flow rate, a differential pressure, a property relating to hematocrit and an orientation of a patient.

2. The system of claim 1, wherein the artificial heart comprises an artificial heart having at least one magnetically levitated component.

3. The system of claim 1, wherein the flow rate comprises positive fluid flow produced by the artificial heart.

4. The system of claim 1, wherein the flow rate comprises negative fluid flow through the artificial heart.

5. The system of claim 1, wherein the differential pressure comprises differential pressure exhibited across an inlet and an outlet of the artificial heart.

6. The system of claim 1, wherein the artificial neural network is further configured to predict a condition of a patient that uses the artificial heart.

7. The system of claim 1, wherein the input vector comprises at least one of rotor speed, rotor position, or motor current of the artificial heart.

8. The system of claim 1, wherein the input vector comprises at least one of levitation current, system current, or system voltage.

9. The system of claim 1, wherein the artificial heart comprises a left ventricular assist device (LVAD).

10. The system of claim 1, wherein the artificial heart comprises a right ventricular assist device (RVAD).

11. The system of claim 1, wherein the neural network is further configured to produce an estimate of a pulsitility index.

12. A computer-implemented method to predict characteristics of an artificial heart using an artificial neural network, comprising:
   receiving, at a computer, an input vector of a predetermined length to train the artificial neural network, the artificial neural network being in communication wits the artificial heart;
   producing, by the artificial neural network, an output vector based on the input vector;
   comparing, by the computer, the output vector with a target vector of the predetermined length;
   when the output vector does not match the target vector within a predetermined error rate, adjusting at least one weight of the artificial neural network;
   when the output vector matches the target vector within the predetermined error rate, executing, by the artificial neural network, the input vector to produce an estimate of at least one of a flow rate, a differential pressure, a property relating to hematocrit and an orientation of a patient.

13. The method of claim 12, wherein producing an estimate comprises producing an estimate if at least one characteristic of an artificial heart that comprise at least one magnetically levitated component.

14. The method of claim 12, wherein the flow rate comprises positive fluid flow produced by the artificial heart.

15. The method of claim 12, wherein the flow rate comprises negative fluid flow through the artificial heart.

16. The method of claim 12, wherein the differential pressure comprises differential pressure exhibited across an inlet and an outlet of the artificial heart.

17. The method of claim 12, further comprising using the artificial neural network to predict a condition of a patient that uses the artificial heart.

18. The method of claim 12, wherein the input vector comprises at least one of rotor speed, rotor position, or motor current of the artificial heart.

19. The method of claim 12, wherein the input vector comprises at least one of levitation current, system current, or system voltage.

20. The method of claim 12, wherein the neural network is further configured to produce an estimate of a pulsitility index.

21. A computer-program product for predicting characteristics of an artificial heart using an artificial neural network, the computer-program product comprising a non-transitory computer-readable medium having instructions thereon, the instructions comprising:
   code programmed to receive an input vector of a predetermined length to train the artificial neural network, the artificial neural network being in communication with the artificial heart;
   code programmed to produce an output vector based on the input vector;
   code programmed to compare the output vector with a target vector of the predetermined length;
   when the output vector does not match the target vector within a predetermined error rate, code programmed to adjust at least one weight;
   when the output vector matches the target vector within the predetermined error rate, code programmed to execute the input vector to produce an estimate of at least one of a flow rate a differential pressure, a property relating to hematocrit and an orientation of a patient.

22. The computer-program product of claim 21, wherein the artificial heart comprises an artificial heart haling at least one magnetically levitated component.

23. The computer-program product of claim 21, wherein the artificial heart comprises a left ventricular assist device (LVAD).

24. The computer-program product of claim 21, wherein the artificial heart comprises a right ventricular assist device (RVAD).

25. A system configured to predict condition of a patient using an artificial heart, comprising:
   a processor;
   memory in electronic communication with the processor; and
   an artificial neural network in communication with the artificial heart, the artificial neural network being configure to:
      receive an input vector of a predetermined length to train the artificial neural network;
      produce an output vector based on the input vector;
      compare the output vector with a target vector of the predetermined length;
      when the output vector does not match the target vector within a predetermined error rate, adjust at last one weight;
      when the output vector matches the target vector within the predetermined error rate, execute the input vector to produce an estimate of at least one of a flow rate, a differential pressure, a property relating to hematocrit and an orientation of a patient.

26. The system of claim 25, wherein the patient uses a natural heart in conjunction with the artificial heart.

27. The system of claim 25, wherein the neural network is further configured to produce an estimate of a pulsitility index of the blood of the patient.

28. The system of claim 27, wherein the pulsitility index describes the strength of a natural heart of the patient being used in conjunction with the artificial heart.

29. The system of claim 25, wherein the neural network is further configured to produce an estimate of blood viscosity properties of the patient.

30. The system of claim 25, wherein the neural network is further configured to produce an estimate of a recovery measurement of the natural heart of the patient.

31. The system of claim 30, wherein the recovery measurement comprises a measurement of the contractility of a native ventricle of the natural heart of the patient.

32. The system of claim 30, wherein the recovery measurement comprises a measurement of the elastance of a native ventricle of the natural heart of the patient.

* * * * *

UNITED STATES PATENT AND TRADEMARK OFFICE
CERTIFICATE OF CORRECTION

PATENT NO. : 8,880,450 B2
APPLICATION NO. : 13/116960
DATED : November 4, 2014
INVENTOR(S) : W. Kurt Dobson et al.

It is certified that error appears in the above-identified patent and that said Letters Patent is hereby corrected as shown below:

IN THE CLAIMS
Column 14, line 19, after "rate" insert -- , --.
Column 14, line 22, delete "haling" and insert therefor -- having --.
Column 14, line 30, "condition" should read -- conditions --.
Column 14, line 37, "figure" should read -- figured --.

Signed and Sealed this
Fifth Day of January, 2016

Michelle K. Lee
*Director of the United States Patent and Trademark Office*